United States Patent [19]

Bare

[11] 4,230,713

[45] Oct. 28, 1980

[54] HETEROCYCLIC TETRAHYDRO-1-ALKYL-4-OXO-1H-IMIDAZOL-2-YLIDENE UREA AND PHENYL ESTERS OF TETRAHYDRO-1-ALKYL-4-OXO-1H-IMIDAZOL-2-YLIDENE CARBAMIC ACID COMPOUNDS

[75] Inventor: Thomas M. Bare, West Chester, Pa.

[73] Assignee: ICI Americas Inc., Wilmington, Del.

[21] Appl. No.: 4,675

[22] Filed: Jan. 19, 1979

[51] Int. Cl.$^3$ .................. C07D 213/75; C07D 233/28; A61K 31/44; A61K 31/415
[52] U.S. Cl. ................... 424/263; 424/273 R; 546/278; 548/309
[58] Field of Search .................. 546/278; 548/309; 424/263, 273 R

[56] References Cited

U.S. PATENT DOCUMENTS 3,983,135   9/1976   Rasmussen .................. 548/309

OTHER PUBLICATIONS

Burger, Medicinal Chemistry, Second Edition, Interscience Publishers, pp. 78–79, 1960.

*Primary Examiner*—Alan L. Rotman

[57] ABSTRACT

Heterocyclic tetrahydro-1-alkyl-4-oxo-1H-imidazol-2-ylidene urea and compounds which are useful as anxiolytic agents in living animals and also some of which act to block acid secretions.

22 Claims, No Drawings

HETEROCYCLIC TETRAHYDRO-1-ALKYL-4-OXO-1H-IMIDAZOL-2-YLIDENE UREA AND PHENYL ESTERS OF TETRAHYDRO-1-ALKYL-4-OXO-1H-IMIDAZOL-2-YLIDENE CARBAMIC ACID COMPOUNDS

This invention relates to certain heterocyclic tetrahydro-1-alkyl-4-oxo-1H-imidazol-2-ylidene urea and phenyl esters of tetrahydro-1-alkyl-4-oxo-1H-imidazol-2-ylidene carbamic acid compounds which have useful anxiolytic activity in living animals and also some of which act to block acid secretions.

The physiologically active compounds of the present invention are represented by the following formulas:

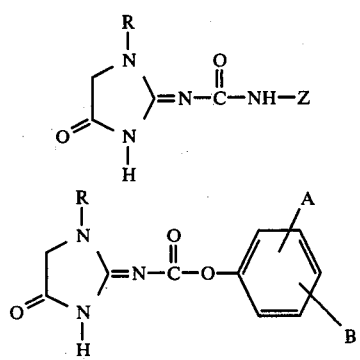

wherein
R is a lower alkyl radical;
Z is a pyridinyl, thienyl or furanyl radical or a pyridinyl, thienyl or furanyl radical substituted with 1 to 3 radicals independently selected from the group consisting of hydroxyl, lower alkoxy, lower alkyl, halogen, nitro (—NO$_2$), NR$^1$R$^2$, CONR$^1$R$^2$, lower haloalkyl, CO$_2$R$^1$ where R$^1$ and R$^2$ are independently selected from hydrogen and lower alkyl;
A and B are independently selected from hydrogen, lower alkyl, halogen, lower alkoxy, lower haloalkyl and nitro.

The term halogen or prefix halo is used herein to represent those halogens having an atomic weight of no more than 127 and include chlorine, fluorine, bromine and iodine.

As used herein (unless otherwise specified) the term "lower alkyl" means a straight or branched chain alkyl radical having from 1 to 8 carbon atoms. Also, the terms "lower alkoxy" and "lower haloalkyl" as used herein mean straight or branched chain alkoxy and haloalkyl radicals respectively having from 1 to 8 carbon atoms, unless otherwise specified.

The compounds of formulas (I) and (II) may be used in the form of pharmaceutically acceptable acid-addition salts. Suitable pharmaceutically acceptable salts include, for example, the hydrochlorides, hydrobromides, phosphates, sulfates, citrates, acetates and maleates.

A more preferred group of compounds of the present invention are those wherein R in formula (I) is a straight or branched chain lower alkyl radical having from 1 to 5 carbon atoms; Z is a pyridinyl, thienyl or furanyl radical or Z is a substituted pyridinyl, thienyl or furanyl radical selected from the group consisting of those represented by the formulas:

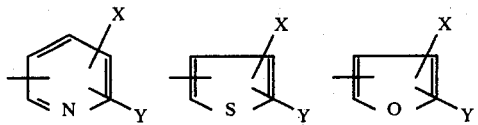

wherein X and Y are radicals independently selected from the group consisting of hydrogen, hydroxyl, straight or branched chain alkoxy having 1 to 5 carbon atoms, straight or branched chain alkyl having 1 to 5 carbon atoms, halogen, nitro, NR$^1$R$^2$, CONR$^1$R$^2$, straight or branched chain haloalkyl having 1 to 5 carbon atoms and CO$_2$R$^1$ where R$^1$ and R$^2$ are independently selected from hydrogen and straight or branched chain alkyl having 1 to 5 carbon atoms.

The compounds of the present invention are further illustrated by the following formulas (III), (IV) and (V) where R, X and Y are as defined hereinabove:

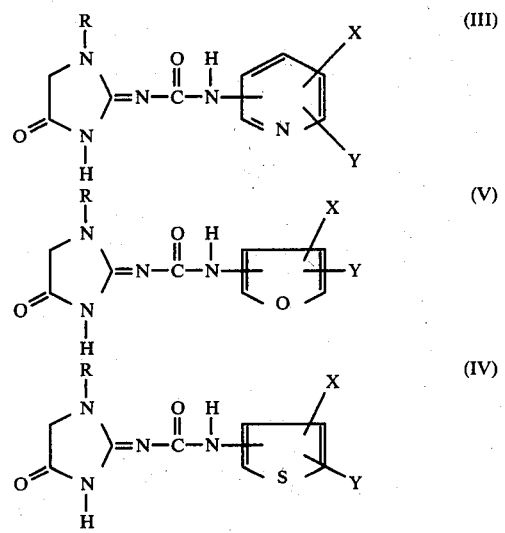

The urea nitrogen of formula (III) which is attached to the pyridine ring may be at the two, three, or four position of the pyridine nucleus and X and Y may be attached to any other open position on the pyridine ring. Similarly, in formulas (IV) and (V) the urea nitrogen may be attached to the two or three position of the thiophene or furan ring and the X and Y substituents attached to any other unoccupied position on the heterocyclic ring. The compounds of formulas (I), (II), (III), (IV) and (V) may also exist in another tautomeric form as depicted in (VI).

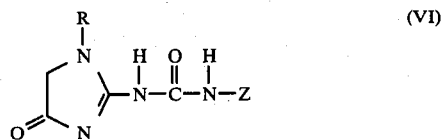

where R and Z are as defined hereinabove.

The compounds of the present invention can be prepared by the following two general procedures.

Procedure 1, as illustrated in the following equations, involves the reaction of one equivalent of the appropriate 2-iminoimidazolidin-4-one 1 with an equivalent amount of an aryl chloroformate 2 in an anhydrous aprotic organic solvent, such as tetrahydrofuran (THF), toluene, and dioxane. An excess of a non-nucleophilic base such as triethylamine, pyridine, sodium carbonate, or the like is also present in the reaction mixture to scavage the liberated hydrogen chloride. The reaction mixture is then stirred at temperatures ranging from 0° to 100° C. for an appropriate time (1-48 hr.), filtered, and the filtrate concentrated to leave the carbamate 3 which is purified by conventional techniques (chromatography, recrystallization, or distillation). It should be noted that the carbamates 3 are also active in the animal tests which are predictive of anxiolytic activity in humans.

The carbamate 3 is then treated with an equimolar, excess, or less than equimolar amount of an appropriate amino-substituted heterocycle 4 or 4a [pyridine 4, thiophene 4a (D=S), or furan 4a (D=O)] either neat or in an anhydrous aprotic solvent such as N,N-dimethylformamide (DMF), THF, dimethylsulfoxide, toluene and other similar organic solvents at temperatures ranging from 25° to 100° C. for 1-48 hours.

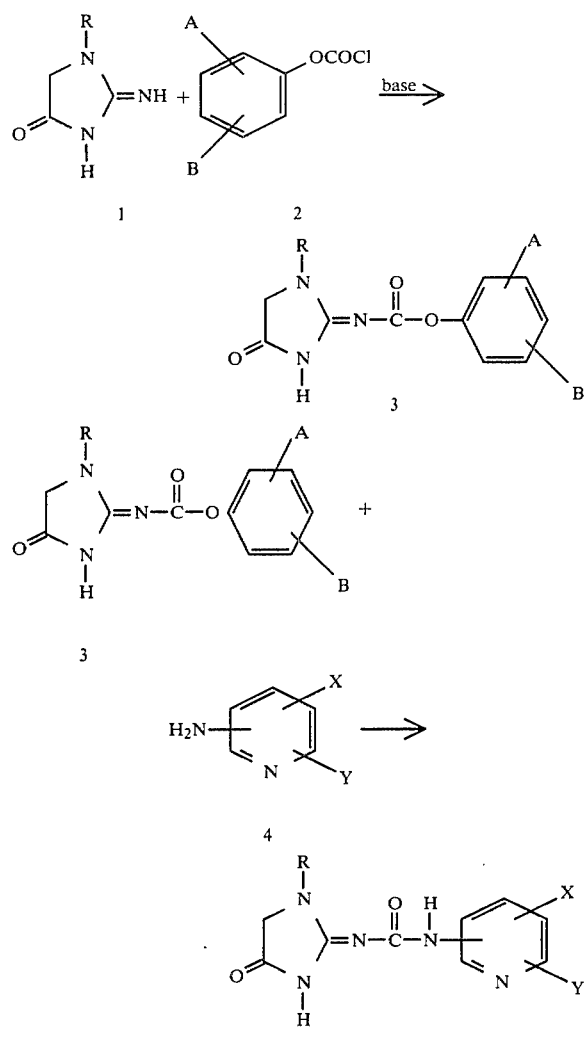

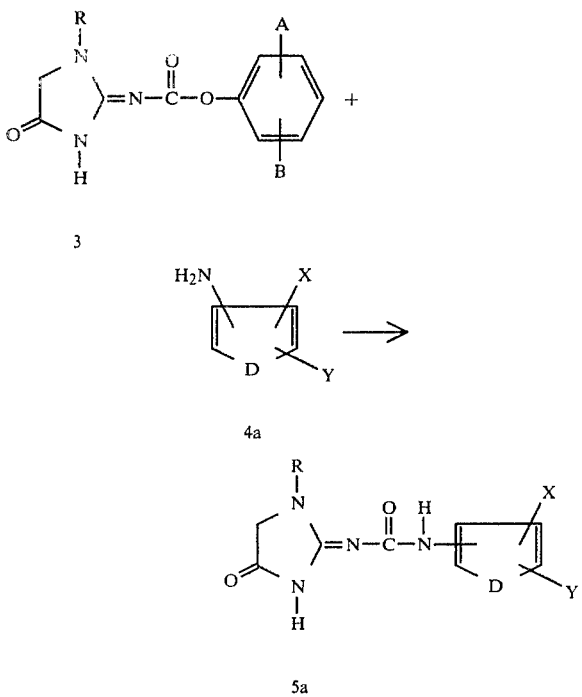

Where R, X and Y represent the same atoms or radicals as described hereinabove;

A = H, straight or branched chain alkyl ($C_1$ to $C_5$), F, Cl, Br, I, straight or branched chain alkoxy ($C_1$ to $C_5$), $CF_3$, $NO_2$;

B = A;

D = O, S;

The product may be isolated by one of two general methods, a and b.

(a) By filtration of the reaction mixture and purification of the collected solid by conventional techniques.

(b) If little or no solid is present at the completion of the reaction, the reaction mixture is poured into a 5-10 fold excess of water. If a precipitate forms, it is collected and purified by conventional techniques. If an oil or no precipitate is evident, the mixture is extracted with a suitable organic solvent (chloroform, ethyl ether, ethyl acetate) and the combined organic extracts are concentrated and the residue purified by conventional means to give the desired product.

Procedure 2, as illustrated in the following equations, involves the reaction of the appropriate 2-iminoimidazolidin-4-one 1 with an equivalent or slight excess of the appropriately substituted heterocyclic isocyanate (6a, 6) in an anhydrous aprotic organic solvent such as DMF, dimethylsulfoxide (DMSO),

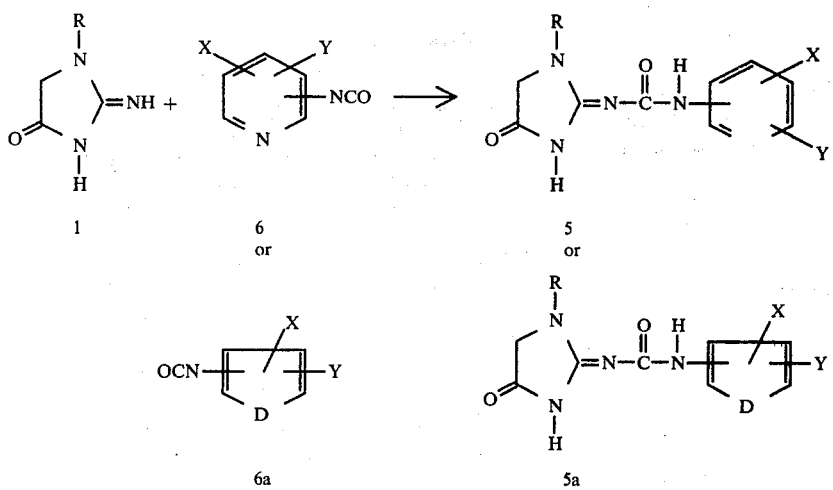

(where R, X, Y and D are as defined previously hereinabove)

THF, toluene or any other similar solvent at temperatures of 25°–100° for 1–10 hours. The product can be isolated by removal of the reaction solvents in vacuo and purification of the residue by conventional techniques or by pouring the reaction mixture into water and collecting the precipitated product. This collected product is purified by conventional procedures.

Several of the heterocyclic isocyanates 6, 6a are known, but, to the extent they are not, they may be prepared by well known methods described in the literature. For example, the procedures described in the following papers may be used to prepare the above isocyanates; J. G. Lombardino and C. F. Gerber, J. Med. Chem. 7, 97 (1964) or H. M. Singleton and W. R. Edwards, Jr., J. Amer. Chem. Soc. 60, 540 (1938).

All of the reactants needed to prepare the compounds of the present invention are commercially available or can be readily prepared by well known methods described in the literature.

Procedure 1 described above is exemplified by the preparation of the following Examples I, III and IV to XIV.

EXAMPLE I 1-(6-methyl-2-pyridinyl)-3-(tetrahydro-1-methyl-4-oxo-1H-imidazol-2-ylidene)urea To a stirred suspension of 50 g (0.44 moles) of creatinine 7 in 600 mls. of anhydrous tetrahydrofuran (THF) was added 49.2 g (0.49 moles) of triethylamine and then dropwise 69.2 g (0.44 moles) of phenyl chloroformate over ½ hour. The mixture was then refluxed for 17 hrs. (hours), cooled and filtered to separate and solid material. The filtrate was concentrated and the residue triturated with 500 ml of ether-hexane (1:1). The solid which formed was chromatographed over silica gel using chloroform as the eluent. The fractions containing the product were combined and concentrated. The residue was again triturated with 500 ml of ether-hexane (1:1) to give 21.2 g of the phenyl ester of tetrahydro-1-methyl-4-oxo-1H-imidazol-2-ylidene carbamic acid, 8, m.p. 129°–132° C.

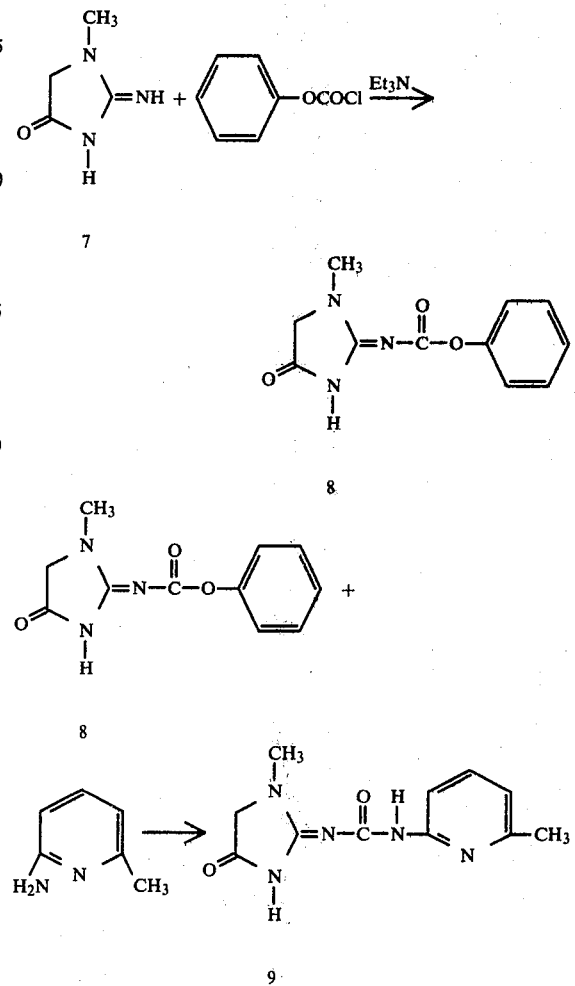

A pure sample of the carbamate 8 was obtained by recrystallization from acetonitrile and a final chromatography over silica gel using chloroformethyl acetate as the eluent. The resulting yellow solid 8 melted at 163°–164° C.

Anal. calcd. for $C_{11}H_{11}N_3O_3$: C, 56.65; H, 4.75; N, 18.02. Found: C, 56.13; H, 4.94; N, 17.86.

To 2.25 g (9.6 mM) of the phenyl carbamate 8 in 10 ml of anhydrous DMF was added 1.04 g (9.6 mM) of 2-amino-6-methylpyridine. After stirring the mixture for 4 hrs. at 50° C., it was filtered to separate a solid which was recrystallized from methanol to give 1.4 g of 1-(6-methyl-2-pyridinyl)-3-(tetrahydro-1-methyl-4-oxo-1H-imidazol-2-ylidene) urea 9 as a white solid, m.p. 202°–203° C. (dec.).

Anal. calcd. for $C_{11}H_{13}N_5O_2$: C, 53.44; H, 5.30; N, 28.32. Found: C, 53.23; H, 5.11; N, 28.23.

Procedure 2 described above is exemplified by the following Examples II and XV to XXIII.

EXAMPLE II

Procedure 2 described above is exemplified by the preparation of 1-(3-pyridinyl)-3-tetrahydro-1-methyl-4-oxo-1H-imidazol-2-ylidene) urea 11. To a solution of 2.13 g (17.8 mM) of 3-pyridinylisocyanate 10 in 30 ml of dimethylformamide was added 2.0 g (17.8 mM) of creatinine 7. The mixture was stirred at 90°–95° C. for 3 hrs. and then cooled to form a precipitate. The solid was collected, washed with ether, and then chromatographed over silica gel using 5% methanol in chloroform as the eluent. The fractions containing the product were combined, treated with charcoal, filtered, and the filtrate diluted with ether to precipitate 1.1 g of 1-(3-pyridinyl)-3-(tetra hydro-1-methyl-4-oxo-1H-imidazol-2-ylidene) urea 11 as pale yellow crystals, m.p. 200°–201° C. (dec.).

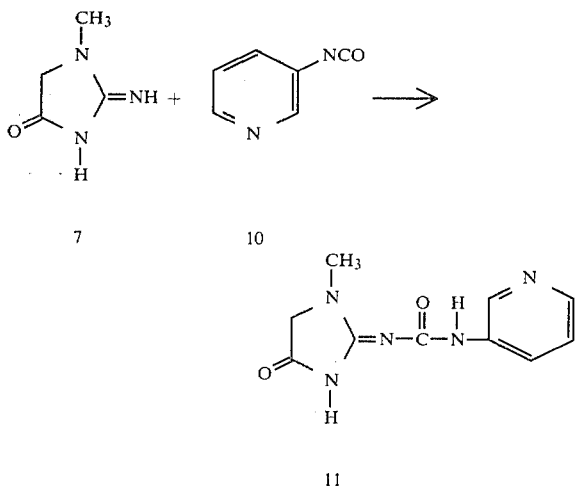

Anal. calcd. for $C_{10}H_{11}N_5O_2$: C, 51.49; H, 4.75; N, 30.03. Found: C, 51.21; H, 4.98; N, 30.04.

EXAMPLE III 1-(2-Pyridinyl)-3-(tetrahydro-1-methyl-4-oxo-1H-imidazol-2-ylidene) urea A mixture of 2.7 g (11.6 mM) of the phenyl ester of tetrahydro-1-methyl-4-oxo-1H-imidazol-2-ylidene carbamic acid 8 and 10.0 g (106 mM) of 2-aminopyridine was heated at 90° C. for 1 hr. The excess amine was removed by vacuum distillation and the residue triturated with 35 ml. ethanol, filtered and the collected solid recrystallized from ethyl acetate to give 1.1 g of the above urea as a cream colored solid, m.p. 218° C. (dec.).

Anal. calcd. for $C_{10}H_{11}N_5O_2$: C, 51.49; H, 4.75; N, 30.03. Found: C, 51.41; H, 4.76; N, 30.09.

EXAMPLE IV 1-(4-Pyridinyl)-3-(tetrahydro-1-methyl-4-oxo-1H-imidazol-2-ylidene) urea A mixture of 4.0 g (17 mM) of the phenyl ester of tetrahydro-1-methyl-4-oxo-1H-imidazol-2-ylidene carbamic acid 8 and 1.6 g (17 mM) of 4-aminopyridine in 25 ml of anhydrous dimethylformamide (DMF) was heated at 55° for 5 hrs. (hours), cooled, and poured with stirring into 250 ml of water. The precipitated solid was collected, washed with ethanol and ether, and air dried. Recrystallization from methanol gave 2.0 g of the above urea as a pale yellow solid, m.p. 218°–220° C. (dec.).

Anal. calcd. for $C_{10}H_{11}N_5O_2$: C, 51.49; H, 4.75; N, 30.03. Found: C, 51.54; H, 4.95; N, 29.92.

EXAMPLE V 1-(4-Methyl-2-pyridinyl)-3-(tetrahydro-1-methyl-4-oxo-1H-imidazol-2-ylidene) urea A mixture of 3.0 g (12.8 mM) of the phenyl carbamate 8 and 2.8 g (25.7 mM) of 2-amino-4-methylpyridine in 25 ml of anhydrous DMF was stirred at 25° C. for 5 hrs., filtered and the filtrate diluted with 150 ml of water. The resulting precipitate was collected and recrystallized from ethanol to give 0.6 g of the above urea as a pale yellow solid, m.p. 231°–232° C. (dec.).

Anal. calcd. for $C_{11}H_{13}N_5O_2$: C, 53.44; H, 5.30; N, 28.32. Found: C, 53.56; H, 5.29; N, 28.39.

EXAMPLE VI 1-(5-Methyl-2-pyridinyl)-3-(tetrahydro-1-methyl-4-oxo-1H-imidazol-2-ylidene) urea A mixture of 2.33 g (10.0 mM) of the phenyl carbamate 8 and 1.08 g (10.0 mM) of 2-amino-5-methylpyridine in 9 ml of anhydrous DMF was stirred at 70° C. for 2 hrs., cooled and poured into water with stirriang. The resulting precipitate was collected, washed with water and then acetone to give 1.9 g of the above urea as a pale yellow solid, m.p. 227° C. (dec.).

Anal. calcd. for $C_{11}H_{13}N_5O_2$; C, 53.43; H, 5.30; N, 28.33. Found: C, 53.64; H, 5.49; N, 28.54.

EXAMPLE VII 1-(4,6-Dimethyl-2-pyridinyl)-3-(tetrahydro-1-methyl-4-oxo-1H-imidazol-2-ylidene) urea A mixture of 3.0 g (12.8 mM) of the phenyl carbamate 8, and 1.6 g (12.8 mM) of 4,6-dimethyl-2-aminopyridine in 50 ml of anhydrous DMF was heated at 55° C. for 8 hrs., cooled, and poured into 200 ml water. The resulting precipitate was collected and recrystallized from ethyl acetate to give 1.3 g of the above urea as a light yellow solid, m.p. 192°–193° C.

Anal. calcd. for $C_{12}H_{15}N_5O_2$: C, 55.16; H, ;b 5.79; N. 26.80. Found: C, 54.99; H, 5.69; N, 26.51.

EXAMPLE VIII 1-(6-Hydroxy-2-pyridinyl)-3-(tetrahydro-1-methyl-4-oxo-1H-imidazol-2-ylidene) urea A mixture of 3.0 g (12.8 mM) of the phenyl carbamate 8 and 1.5 g (12.8 mM) of 2-amino-6-hydroxypyridine in 25 ml of anhydrous DMF was heated at 85° C. for 5 hrs., cooled, and poured into 100 ml of water. The resulting precipitate was collected, washed successively with water, ethanol, ethyl acetate, and ether. Recrystallization from ethanol gave 1.0 g of the above urea as a yellow solid, m.p. 233°–234° C. (dec.).

Anal. calcd. for $C_{10}H_{11}N_5O_3$: C, 48.19; H, 4.45; N, 28.10. Found: C, 48.04; H, 4.71; N, 28.14.

EXAMPLE IX 1-(2-Methoxy-5-pyridinyl)-3-(tetrahydro-1-methyl-4-oxo-1H-imidazol-2-ylidene) urea A mixture of 2.33 g (10.0 mM) of phenyl carbamate 8 and 1.24 g. (10.0 mM) of 5-amino-2-methoxypyridine in 9 ml of anhydrous DMF was heated at 70° C. for 6 hrs., cooled, and poured into 40 ml of water. On cooling in ice, crystals precipitated from the aqueous solution and these were collected and recrystallized from methanol to give 0.5 g of the above urea as pale yellow needles, m.p. 175°–176° C.

Anal. calcd. for $C_{11}H_{13}N_5O_3$: C, 50.18; H, 4.98; N, 26.61. Found: C, 49.98; H, 5.14; N, 26.92.

EXAMPLE X 1-(5-Chloro-2-pyridinyl)-3-(tetrahydro-1-methyl-4-oxo-1H-imidazol-2-ylidene) urea A mixture of 2.3 g. (10 mM) of the phenyl carbamate 8 and 3.0 g. (23 mM) of 2-amino-5-chloropyridine in 25 ml of anhydrous DMF was heated at 45°–50° C. for 2 hrs., cooled and filtered. The collected solid was washed successively with cold DMF, ethyl acetate, and ether to give 1.6 g of the above urea as a yellow solid, m.p. 250°–251° C. (dec.).

Anal. calcd. for $C_{10}H_{10}ClN_5O_2$: C, 44.87; H, 3.77; N, 26.16; Cl, 13.25. Found: C, 44.77; H, 3.95; N, 26.22; Cl, 13.21.

EXAMPLE XI 1-(5-Nitro-2-pyridinyl)-3-(tetrahydro-1-methyl-4-oxo-1H-imidazol-2-ylidene) urea A mixture of 3.0 g (12.8 mM) of the phenyl carbamate 8 and 1.8 g (12.8 mM) of 2-amino-5-nitropyridine in 20 ml of anhydrous DMF was stirred at 25° C. for 2 days. The reaction mixture was filtered and the collected solid washed successively with cold DMF, ethyl acetate, and ether to give 1.0 g of the above urea as yellow solid, m.p. 225°–227° C. (dec.).

Anal. calcd. for $C_{10}H_{10}N_6O_4$: C, 43.17; H, 3.62; N, 30.20. Found: C, 43.27; H, 3.93; N, 30.59.

EXAMPLE XII 1-(5-Aminocarbonyl-2-pyridinyl)-3-(tetrahydro-1-methyl-4-oxo-1H-imidazol-2-ylidene) urea A mixture of 1.00 g (4.29 mM) of the phenyl carbamate 8 and 0.59 g (4.29 mM) of 6-aminonicotinamide in 4 ml of anhydrous DMF was stirred at 65° C. for 1.5 hr., cooled and poured into water. The resulting precipitate was collected, washed with acetone and air dried to give 0.85 g of the above urea as a pale yellow solid, m.p. 240°–243° C. (dec.).

Anal. calcd. for $C_{11}H_{12}N_6O_3$: C, 47.82 Found: C, 47.83.

EXAMPLE XIII 1-(3-Methyl-2-pyridinyl)-3-(tetrahydro-1-methyl-4-oxo-1H-imidazol-2-ylidene) urea A mixture of 5.0 g (21.4 mM) of the phenyl carbamate 8 and 1.2 g (10.7 mM) of 2-amino-3-methyl-pyridine in 25 ml of anhydrous DMF was heated at 55° for 3 hrs. and then cooled. The solid was collected via filtration and washed successively with cold DMF, ethyl acetate and ether. Recrystallization from ethanol and a final wash with water gave 0.07 g of the above urea as a pale yellow solid, m.p. 219°–221° C. (dec.).

Anal. calcd. for $C_{11}H_{13}N_5O_2$: C, 53.43; H, 5.30; N, 28.32. Found: C, 53.32; H, 5.36; N, 28.51.

EXAMPLE XIV 1-(2-Dimethylamino-5-pyridinyl)-3-(tetrahydro-1-methyl-4-oxo-1H-imidazol-2-ylidene) urea A mixture of 8.1 g (35 mM) of the phenyl carbamate 8 and 2.5 g (23 mM) of 5-amino-2-dimethylaminopyridine in 50 ml of anhydrous DMF was heated at 55° for 3.5 hrs. and then cooled and poured into 200 ml of water. The resulting mixture was extracted with three 100 ml portions of ethyl acetate and the combined extracts were dried (MgSO4), filtered and concentrated to a volume of 50 ml. The precipitate which formed was collected and recrystallized from acetone to give 0.84 of the above urea as tan crystals, m.p. 212°–213° C.

Anal. calcd. for $C_{12}H_{16}N_6O_2$: C, 52.17; H, 5.84; N, 30.42. Found: C, 52.04; H, 5.88; N, 30.07.

EXAMPLE XV 1-(Tetrahydro-1-methyl-4-oxo-1H-imidazol-2-ylidene)-3-(2-thienyl) urea To 9.4 g (83 mM) of creatinine in 100 ml of anhydrous DMF was added with stirring of solution of 9.2 g (75 mM) 2-thienyl isocyanate in 60 ml of toluene. After the addition was completed, the mixture was stirred at 55° C. for 1 hr., cooled, and the solvents removed in vacuo. The residue was recrystallized first from ethanol and then ethyl acetate (treated with charcoal) to give 5.3 g of the above urea as an off-white solid, m.p. 191°–192° C. (dec.).

Anal. calcd. for $C_9H_{10}N_4O_2S$: C, 45.37; H, 4.23; N, 23.51. Found: C, 45.46; H, 4.40; N, 23.59.

EXAMPLE XVI 1-(Tetrahydro-1-methyl-4-oxo-1H-imidazol-2-ylidene)-3-(3-thienyl) urea To a stirred suspension of 2.6 (23 mM) of creatinine in 50 ml of anhydrous DMF was added a solution of 3.0 g (23 mM) of 3-thienyl isocyanate in 25 ml of toluene. The resulting mixture was heated at 75° C. for 4.5 hrs., cooled and added to 150 ml of water. The resulting precipitate was collected and recrystallized from ethyl acetate to give 1.4 g of the above urea as a cream colored solid, m.p. 194°–195° C.

Anal. calcd. for $C_9H_{10}N_4O_2S$: C, 45.37; H, 4.23; N, 23.51. Found: C, 44.96; H, 4.39; N, 23.67.

EXAMPLE XVII 1-(4-Chloro-2-thienyl)-3-(tetrahydro-1-methyl-4-oxo-1H-imidazol-2-ylidene) urea To 3.0 g (26.5 mM) of creatinine in 50 ml of anhydrous DMF was added with stirring a solution of 4-chloro-2-thienyl isocyanate in 25 ml of toluene. After stirring at 65° C. for 5 hrs., the mixture was cooled, added to 200 ml of water and filtered to separate a precipitate, which was recrystallized from ethanol and then ethyl acetate to give 1.0 g of the above urea as a light tan solid, m.p. 203°–204° C. (dec.) containing $\frac{1}{8}$ mole of ethyl acetate of recrystallization.

Anal. calcd. for $C_9H_9N_4ClO_2S \cdot \frac{1}{8} C_4H_8O_2$: C, 40.22; H, 3.55; N, 19.75. Found: C, 40.10; H, 3.84; N, 20.02.

EXAMPLE XVIII 1-(5-Methyl-2-thienyl)-3-(tetrahydro-1-methyl-4-oxo-1H-imidazol-2-ylidene) urea To 1.44 g (12.8 mM) of creatinine in 25 ml of anhydrous DMF was added with stirring 1.78 g (12.8 mM) of 5-methyl-2-thienyl isocyanate in 12 ml of toluene. After 6 hrs. at 60° C., the mixture was cooled, poured into 100 ml of water and filtered. The collected solid was recrystallized twice from ethyl acetate to give 2.4 g of the above urea as a yellow-orange solid, m.p. 207°–209° C.

Anal. calcd. for $C_{10}H_{12}N_4O_2S$: C, 47.61; H, 4.79; N, 22.21. Found: C, 47.57; H, 4.76; N, 22.31.

EXAMPLE XIX 1-(3-Methyl-2-thienyl)-3-(tetrahydro-1-methyl-4-oxo-1H-imidazol-2-ylidene) urea To a stirred suspension of 3.0 g (26.0 mM) of creatinine in 50 ml of anhydrous DMF was added dropwise a solution of 3.7 g (26 mM) of 3-methyl-2-thienyl isocyanate in 35 ml of toluene. After stirring at 90° C. for 6 hrs., the reaction mixture was cooled and poured into 100 ml of water. The separated solid was collected, washed with water and recrystallized from ethyl acetate to give 1.2 g of the above urea as a grey-white solid, m.p. 201°–202° C.

Anal. calcd. for $C_{10}H_{12}N_4O_2S$: C, 47.61; H, 4.79; N, 22.21. Found: C, 47.76; H, 4.83; N, 22.25.

EXAMPLE XX 1-(5-Bromo-2-thienyl)-3-(tetrahydro-1-methyl-4-oxo-1H-imidazol-2-ylidene) urea To a stirred suspension of 3.0 g (26 mM) of creatinine in 30 ml of anhydrous DMF was added a solution of 5.0 g (26.5 mM) of 5-bromo-2-thienyl isocyanate in 15 ml of toluene. The resulting mixture was heated at 75° C. for 3 hrs., cooled, and poured into 200 ml of water. The precipitate was collected, washed with ethanol and ether, and air-dried. The solid was dissolved in 250 ml hot acetone, treated with charcoal, filtered, and the filtrate diluted with water (250 ml). The resulting precipitate was collected, washed with acetone and then ether. Air-drying gave 2.3 g of the above urea as a buff powder, m.p. 192°–193° C. (dec.).

Anal. calcd. for $C_9H_9BrN_4O_2S$: C, 34.08; H, 2.86; N, 17.66. Found: C, 33.94; H, 3.04; N, 17.30.

EXAMPLE XXI 1-(5-Methoxy-2-thienyl)-3-(tetrahydro-1-methyl-4-oxo-1H-imidazol-2-ylidene) urea To a stirred suspension of 3.0 g (26 mM) of creatinine in 25 ml of anhydrous DMF was added a solution of 4.1 g (26 mM) of 5-methoxy-2-thienyl isocyanate in 20 ml of toluene. The resulting mixture was heated at 65° C. for 4.5 hrs., cooled, and poured into 200 ml of water. The mixture was extracted with ethyl acetate, and the combined extracts dried ($MgSO_4$) and concentrated. The residue was recrystallized from ethyl acetate and then ethanol. Final purification was accomplished by chromatography over silica gel (ethyl acetate as eluant), decolorizing the product with charcoal, concentration and recrystallization from acetone-hexane to give 0.23 g of the above urea as a light brown solid, m.p. 180°–182° C. (dec.).

Anal. calcd. for $C_{10}H_{12}N_4O_3S$: C, 44.78; H, 4.51; N, 20.88. Found: C, 44.71; H, 4.67; N, 20.88.

EXAMPLE XXII 1-(2-Furanyl)-3-(tetrahydro-1-methyl-4-oxo-1H-imidazol-2-ylidene) urea To a stirred mixture of 6.9 g (60 mM) of creatinine in 100 ml of anhydrous DMF was added a solution of 6.5 g (60 mM) of 2-furanyl isocyanate in 75 ml of toluene. After stirring the mixture 1 hr. at 25° C. and then 1 hr. at 55° C., the solvents were removed in vacuo and the residue taken up in ethyl acetate and washed with water. The solvent was removed and the residue chromatographed over silica gel using ether-ethyl acetate (4:1) as the eluant. The fractions containing the product were combined and concentrated to leave 1.1 g of the above urea as an off-white solid, m.p. 173°–175° C. (dec.)

Anal. calcd. for $C_9H_{10}N_4O_3$: C, 48.65; H, 4.53; N, 25.21. Found: C, 48.54; H, 4.72; N, 24.92.

EXAMPLE XXIII 1-(3-Furanyl)-3-(tetrahydro-1-methyl-4-oxo-1H-imidazol-2-ylidene) urea To a stirred mixture of 18.3 g (162 mM) of creatinine in 120 ml of anhydrous DMF was added a solution of 17.2 g (162 mM) of 3-furanyl isocyanate in 80 ml of toluene. After stirring the mixture for 3 hrs. at 65° C., the mixture was partially concentrated under vacuum and the residue poured into 1200 ml of water. The resulting precipitate was collected, washed with water and recrystallized from ethyl acetate. The solid was then chromatographed over silica gel using ethyl acetate as the eluant and the fractions containing the product were concentrated and the residue recrystallized from toluene to give 0.5 g of the above urea as a tan solid, m.p. 179°–181° C. (dec.).

Anal. calcd. for $C_9H_{10}N_4O_3$: C, 48.65; H, 4.53; N, 25.21. Found: C, 48.85; H, 4.68; N, 25.17.

To further illustrate the preparation of the compounds of the present invention 1-(tetrahydro-1-methyl-4-oxo-1H-imidazol-2-ylidene)-3-(6-trifluoromethyl-2-pyridinyl)urea, 1-(4-chloro-6-methyl-2-pyridinyl)-3-(tetrahydro-1-ethyl-4-oxo-1H-imidazol-2-ylidene)urea, 1-(5-carboxyl-2-pyridinyl)-3-(tetrahydro-1-isopropyl-4-oxo-1H-imidazol-2-ylidene)urea, and 1-(2-pyridinyl)-3-(tetrahydro-1-pentyl-4-oxo-1H-imidazol-2-ylidene)urea can be prepared by the method of Example VI by using the equivalent amount of the appropriate phenyl ester of tetrahydro-1-alkyl-4-oxo-1H-imidazol-2-ylidene carbamic acid and the appropriate substituted aminopyridine as reactants.

1-(3-methyl-2-furanyl)-3-(tetrahydro-1-ethyl-4-oxo-1H-m imidazol-2-ylidene)urea, 1-(tetrahydro-1-isopropyl-4-oxo-1H-imidazol-2-ylidene)-3-(3-thienyl)urea, 1-(tetrahydro-1-ethyl-4-oxo-1H-imidazol-2-ylidene)-3-(2-thienyl)urea, 1-(4-chloro-2-furanyl)-3-(tetrahydro-1-methyl-4-oxo-1H-imidazol-2-ylidene)urea, 1-(5-carbomethoxy-2-thienyl)-3-tetrahydro-1-methyl-4-oxo-1H-imidazol-2-ylidene)urea, 1-(tetrahydro-1-methyl-4-oxo-1H-imidazol-2-ylidene)-3(2-trifluoromethyl-4-furanyl-)urea, 1-(4-pentafluoroethyl-2-furanyl)-3-(tetrahydro-1-n-propyl-4-oxo-1H-imidazol-2-ylidene)urea, and 1-(5-aminocarboxyl-2-thienyl)-3-(tetrahydro-1-ethyl-4-oxo-1H-imidazol-2-ylidene)urea can be prepared by the process of Example XVIII by using the equivalent amount of the appropriate 1-alkyl-2-iminoimidazolidin-4-one and the appropriate substituted thienyl or furanyl isocyanate as reactants.

The following Examples XXIV to XXVII further illustrate the present invention:

EXAMPLE XXIV

1-(3-Bromo-2-thienyl)-3-(tetrahydro-1-methyl-4-oxo--1-H-imidazol-2-ylidene) urea To a stirred suspension of 0.8 g (7.1 mM) of creatinine in 10 ml of anhydrous DMF was added a solution of 1.12 g (5.5 mM) of 3-bromo-2-thienyl isocyanate in 5 ml of toluene. The resulting mixture was heated at 65° C. for 5 hrs. (hours), cooled, and poured into a mixture of 200 ml water and 25 ml toluene. The precipitate was collected and recrystallized from ethyl acetate to give 0.36 g of the above urea as a tan colored solid, m.p. 192°-193° C. (dec.)

Anal. calcd. for $C_9H_9BrN_4O_2S$: C, 34.08; H, 2.86; N, 17.66. Found: C, 33.95; H, 2.86; N, 17.59.

EXAMPLE XXV

1-(2-Chloro-4-thienyl)-3-(tetrahydro-1-methyl-4-oxo-1H-imidazol-2-ylidene) urea To a stirred suspension of 2.5 g (22.5 mM) of creatinine in 30 ml of anhydrous DMF was added a solution of 2.87 g (18 mM) of 2-chloro-4-thienyl isocyanate in 20 mls toluene. The resulting mixture was heated at 80° C. for 3.5 hrs., cooled, and poured into a mixture of 250 ml of water and 50 ml toluene. The precipitate was collected and recrystallized from ethyl acetate to give 1.5 g of the above urea as a tan solid, m.p. 198°-200° C.

Anal. calcd. for $C_9H_9N_4Cl\ O_2S$: C, 39.64; H, 3.33; N, 20.54. Found: C, 39.55; H, 3.33; N, 20.70.

EXAMPLE XXVI

1-(5-Chloro-2-thienyl)-3-(tetrahydro-1-methyl-4-oxo-1H-imidazol-2-ylidene) urea To a stirred suspension of 2.5 g (22.5 mM) of creatinine in 30 ml of anhydrous DMF was added a solution of 2.87 g (18 mM) of 5-chloro-2-thienyl isocyanate in 15 ml of toluene. The resulting mixture was heated at 80° C. for 3.5 hrs., cooled, and poured into a mixture of 250 ml of water and 50 ml of toluene. The precipitate was collected and recrystallized from ethyl acetate to give 1.5 g of the above urea as a tan solid, m.p. 204°-205° C.

Anal. calcd. for $C_9H_9N_4Cl\ O_2S$: C, 39.64; H, 3.33; N, 20.54. Found: C, 39.56; H, 3.45; N, 20.31.

EXAMPLE XXVII

1-(2-Nitro-4-thienyl)-3-(tetrahydro-1-methyl 4-oxo-1H-imidzol-2-ylidene) urea To a stirred suspension of 1.4 g (12.5 mM) of creatinine in 40 ml of anhydrous DMF was added a solution of 1.7 g (10 mM) of 2-nitro-4-thienyl isocyanate in 20 ml of toluene. The resulting mixture was heated at 90° C. for 5 hrs., cooled and poured into a mixture of 250 ml water and 50 ml toluene. The precipitate was collected, washed with toluene, and recrystallized from acetone to give 0.5 g of the above urea as a bright yellow solid, m.p. 221°-222° C. (dec.).

Anal. calcd. for $C_9H_9N_5O_4S$: C, 38.16; H, 3.20; N, 24.72. Found: C, 38.04; H, 3.39; N, 24.68.

As indicated above, the compounds of the present invention are considered to be useful in the treatment of anxiety in living animal bodies particularly mammals.

The general class of compounds known as the benzodiazepines is widely prescribed for the treatment of anxiety. These compounds are excellent anxiolytic agents, but do have associated with them a number of ancillary activities such as sedation, muscle relaxation, anti-convulsant and hypnotic properties. Since the benzodiazepines are central nervous system depressants, they also potentiate the depressant effects of alcohol and other depressants such as the barbiturates; consequently, patients using the benzodiazepines must be warned against mixing excessive doses of these compounds with alcohol and of the additive effects of sedative drugs. In the animal laboratory the Geller-Seifter Conflict test and the Shock-Induced Supression of Drinking (SSD) test are considered good laboratory models for human anxiety. The sedative and muscle relaxant component of the benzodiazepines can be correlated with a general central nervous system (CNS) battery screen which includes the forced motor activity (FMA) test (to measure neuromuscular impairment) and several anti-convulsant tests (strychnine, metrazol, electroshock) which gave an indication of muscle relaxant activity. Therefore, any anxiolytic agent (as determined by the Geller-Seifter or SSD tests) can also be tested for potential sedative and muscle relaxant side-effects by using the CNS battery. Obviously, anxiolytic agents which have good activity in the Geller-Seifter or SSD tests and a low degree of sedative and muscle relaxant effects as measured by the CNS battery would be the compounds which are desired. In standard laboratory tests the compounds of the present invention, in general, as described herein demonstrate their ability to fulfill this goal, i.e., anxiolytic activity with little or not sedative action.

Among the tests conducted to demonstrate the anxiolytic activity of the present compounds was the Shock-Induced Suppression of Drinking (Rats) (SSD) Test which was carried out as follows:

Male rats in the weight range of 250 to 280 grams are water-deprived for 48 hours and food-deprived for 24 hours before testing. The rats are orally intubated (5 ml/kg) with the test compound (based on mg/kg body weight). The vehicle control group of rats is also intubated by mouth. A positive control group of rats is also orally administered a control dose of 18 mg/kg of chlordiazepoxide. Randomization is utilized in dosing. The rats are returned to the cage for one hour. Sixty minutes after drug administration, the rat is quietly removed from its cage and the hind feet wiped with a 10% solution of EEG electrode cream. The rat is placed on the floor in the chamber facing the licking tube. The animal is allowed 5 minutes to make 20 licking responses and receive the first shock (0.5 mA). If this does not occur, and animal is removed and eliminated from the study. If 20 licking responses are made, the animal is permitted an additional 3 minutes during which time each 20th lick is paired with a 0.5 mA shock. This period is automatically started, counted, and terminated. The number of licks and shocks are recorded. The activity of the compound tested is evaluated by comparing the mean shocks of the group dosed with the test compound to both the mean shocks of the vehicle and positive control groups. The higher the number of shocks received the higher the anti-conflict or anti-anxiety activity the compound has.

In general, testing of the compounds of the present invention in rats in the above described SSD test indicates that the effective anxiolytic dosage of the subject compounds represented by formulas (I) and (II) in living animals, when administered orally, is from about 5 mg/kg to 200 mg/kg body weight with a more preferred range being from about 7 mg/kg to 100 mg/kg body weight.

The compound of Example XV, which is a preferred compound, exhibited about the same level of activity in the above described SSD test when administered at 25 mg/kg body weight as chlordiazepoxide when administered at 18 mg/kg body weight. The compound of Example XVI, another preferred compound, when dosed at 12.5 mg/kg body weight in the SSD test demonstrated about the same level of activity as chlordiazepoxide administered at 18 mg/kg.

Based on the activitites of the present heterocyclic tetrahydro-1-alkyl-4-oxo-1H-imidazol-2-ylidene urea and carbamate compounds of Formula (I) and (II) above demonstrated in standard animal tests and a comparison of these with the activities of the present known anxiolytic agents in the same tests, it is concluded that the pharmaceutical compositions of this invention may, in general, be administered to man for the treatment of anxiety at an oral dose of between about 5 mg and 500 mg of active ingredient, the composition being administered 1 to 4 times a day. A more preferred oral dosage for man is considered to be from about 5 mg to 250 mg of active ingredient 1 to 4 times a day. It will, however, be appreciated that the amount of the present heterocyclic tetrahydro-1-alkyl-4-oxo-1H-imidazol-2-ylidene urea and carbamate compounds administered will vary depending on the degree of anxiety to be dealt with and the compound used.

Some of the subject compounds tested were also found to block acid secretion under the standard laboratory test procedure -the pyloris ligated rat (Shay Rat, WSR). Under the test utilized, five (5) rats each weighing about 170 grams are dosed with each compound to be tested at a dose of 50 milligrams per kilogram body weight. 59.5 milligrams of each drug to be tested is dispersed in 7 milliliters of an aqueous solution containing 0.5% weight/volume of hydroxypropylmethylcellulose and 0.1% weight/volume of TWEEN 80 polyoxyethylene(20)sorbitan monooleate. One milliliter of this resulting dispersion containing a compound to be tested is given intraduodenally to each of five (5) rats to be tested at the time of surgery. The rats are anesthetized with 37.5 milligrams per kilogram body weight of Brevital (methohexital sodium) given by interperitoneal injection. An incision about one inch long is made in the center of the abdomen of the rat going caudal from the base of the sternum. The incision is made with a scalpel in mid-line through to the body cavity. The duodenum is pulled through the open wound until the pyloric area is out. Then a nylon tie is placed under the antral stomach just above the pylorus and pulled tight to create a sticture. The intestines are then replaced in the body cavity and the wound closed with a wound clipper followed by a liberal painting with collodion. After a 4 hour period each rat is sacrificed by cervical dislocation and the stomach was pulled out by the esophagus gripped by a hemostat. The stomach is then cut away from the intestine and membranes from the other end of the stomach and the stomach is cut open along the greater curviture while holding above a funnel positioned above a graduated centrifuged tube to collect the content of the stomach. The material is centrifuged at top speed for 8 to 12 minutes and an aliquot portion is titrated to determine the acid concentration and total acid output. A control of five rats not dosed with a drug but given the vehicle is run with each group of rats compounds tested. Results are reported in percent inhibition versus the controls.

The compounds of Examples I, XV and XVII when tested according to the above described procedure exhibited very significant acid anti-secretory activity. The compounds of Examples III and IV did not exhibit significant activity at this dosage; however, it is considered that they are active at a higher dosage. In general, based on test results it is considered that the effective acid blocking dosage of the compounds of this invention when administered orally is from about 10 mg/kg to 200 mg/kg body weight preferably from 10 mg/kg to 100 mg/kg body weight.

As the compounds within the scope of this invention are effective upon oral administration, they can be compounded into any suitable oral dosage form, such as in tablet, capsule, syrup, elixir, suspension or other solid or liquid forms that can be prepared by procedure well known in the art. Thus, the subject novel compounds can be mixed with a suitable diluent, such as lactose or kaolin, and encapsulated; or they can be combined with suitable binding agents and expanding agents and compressed into tablets. In addition, a liquid pharmaceutical may be obtained by dissolving, dispersing, or suspending novel compounds of this invention with a suitable flavored liquid. The present compounds are also considered active upon parenteral and rectal administration.

Examples of formulations for preparing tablets, capsules, liquids, parenterals, and suppositories containing the compounds of the present invention are described below. Obviously, it will be recognized by one skilled in the present art that they following formulations represent only one method of preparing such pharmaceutical compositions and obviously the size of the tablet or capsule or the strength of the dosage form may be suitably varied in order to satisfy the particular requirements, such as dosage level indicated. For example, each dosage unit may conveniently contain from about 1 milligram to about 50 milligrams of the active ingredient admixed with a diluent amount of a pharmaceutically acceptable carrier. Any of the well known suitable pharmaceutical carriers can be used to prepare acceptable dosage forms so as to provide an effective amount or therapeutically effective amount of the compound to be administered.

| Suspension Containing 50 mg per 5 cc of 1-(Tetrahydro-1-methyl-4-oxo-1H-imidazol-2-ylidene)-3-(2-thienyl) urea | |
| --- | --- |
| 1-(Tetrahydro-1-methyl-4-oxo-1H-imidazol-2-ylidene)-3-(2-thienyl) urea | 10.0 grams |
| Tragacanth | 25 grams |
| Syrup Cherry | 60 ml |
| Distilled Water. q.s. | 100 ml |

Hydrate the tragacenth with sufficient water to form a smooth paste and to this add the 1-(Tetrahydro-1-methyl-4-oxo-1H-imidazol-2-ylidene)-3-(2-thienyl)urea. Then add the syrup of cherry and distilled water to make 1000 ml.

| Capsule Containing 25 mg of 1-(3-pyridinyl)-3-tetrahydro-1-methyl-4-oxo-1H-imidazol-2-ylidene) urea | |
| --- | --- |
| 1-(3-pyridinyl)-3-tetrahydro-1-methyl-4-oxo-1H-imidazol-2-ylidene) urea | 25 mg |

| Capsule Containing 25 mg of 1-(3-pyridinyl)-3-tetrahydro-1-methyl-4-oxo-1H-imidazol-2-ylidene) urea |  |
|---|---|
| Powdered Lactose | 350 mg |
| D.T.D. Capsules No. 1000 |  |

Mix the ingredients so as to evenly distribute the active ingredient throughout the lactose. Pack the powder into a No. 1 empty gelatin capsule.

| Tablet Containing 50 mg of 1-(6-methyl-2-pyridinyl)-3-tetrahydro-1-methyl-4-oxo-1H-imidazol-2-ylidene) urea |  |
|---|---|
| 1-(6-methyl-2-pyridinyl)-3-tetrahydro-1-methyl-4-oxo-1H-imidazol-2-ylidene) urea | 50 grams |
| Starch | 160 grams |
| Powdered Lactose | 160 grams |
| Talc | 20 grams |
| Weight of Granulation | 390 grams |

Combine all ingredients, mix, and then compress into slugs. The slugs should then be ground to form granules that will pass through a 14 to 16 mesh screen. The granules may then be recompressed into 1000 tablets using a suitable compression mold to form tablets, each weighing 345 mg.

| Injectable Containing 40 mg of 1-(Tetrahydro-1-methyl-4-oxo-1H-imidazol-2-ylidene)-3-(3-thienyl) urea |  |
|---|---|
| 1-(Tetrahydro-1-methyl-4-oxo-1H-imidazol-2-ylidene)-3-(3-thienyl) urea | 40.0 grams |
| Chlorobutanol | 3.0 grams |
| Propylene Glycol | 40.0 grams |
| Water for Injection, q.s. | 1000.0 ml |

Combine the above ingredients, clarify by filtration, fill into vials, seal, and autoclave.

What is claimed is:

1. A compound selected from the group consisting of those represented by the following formula (I):

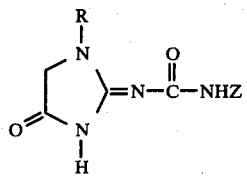

wherein
R is a lower alkyl radical;
Z is a 2- or 4-pyridinyl, thienyl, furanyl, 6-lower alkyl-2-pyridinyl or 2-halogen-4-thienyl radical or a furanyl radical substituted with one substituent selected from the group consisting of hydroxyl, lower alkoxy, lower alkyl, halogen, nitro, $NR^1R^2$, $CONR^1R^2$, lower haloalkyl and $CO_2R^1$ where $R^1$ and $R^2$ are independently selected from hydrogen and lower alkyl;
or a pharmaceutically acceptable acid-addition salt thereof.

2. A compound of claim 1 wherein R is a lower alkyl radical having from 1 to 5 carbon atoms.

3. A compound of claim 2 wherein Z is a radical selected from the group consisting of 2- or 4-pyridinyl, thienyl and furanyl.

4. A compound of claim 2 wherein Z is furanyl substituted with one substituent selected from the group consisting of hydrogen, hydroxyl, straight or branched chain alkoxy having 1 to 5 carbon atoms, straight or branched chain alkyl having 1 to 5 carbon atoms, halogen, nitro, $NR^1R^2$, $CONR^1R^2$, straight or branched chain haloalkyl having 1 to 5 carbon atoms and $CO_2R^1$ where $R^1$ and $R^2$ are independently selected from hydrogen and straight or branch chain alkyl having 1 to 5 carbon atoms.

5. A compound of claim 1 wherein R is methyl and Z is 2- or 4-pyridinyl.

6. A compound of claim 1 wherein R is methyl and Z is thienyl.

7. A compound of claim 1 wherein R is methyl and Z is furanyl.

8. A compound of claim 1 which is 1-(6-methyl-2-pyridinyl)-3-(tetrahydro-1-methyl-4-oxo-1H-imidazol-2-ylidene) urea.

9. A compound of claim 1 which is 1-(2-Pyridinyl)-3-(tetrahydro-1-methyl-4-oxo-1H-imidazol-2-ylidene) urea.

10. A compound of claim 1 which is 1-(4-Pyridinyl)-3-(tetrahydro-1-methyl-4-oxo-1H-imidazol-2-ylidene) urea.

11. A compound of claim 1 which is 1-(Tetrahydro-1-methyl-4-oxo-1H-imidazol-2-ylidene)-3-(2-thienyl) urea.

12. A compound of claim 1 which is 1-(Tetrahydro-1-methyl-4-oxo-1H-imidazol-2-ylidene)-3-(3-thienyl) urea.

13. A compound of claim 1 which is 1-(2-Furanyl)-3-(tetrahydro-1-methyl-4-oxo-1H-imidazol-2-ylidene) urea.

14. A pharmaceutical composition for the treatment of anxiety comprising a therapeutically effective amount of a compound of claim 1 in combination with a pharmaceutically acceptable carrier or diluent therefor.

15. A method for the treatment of anxiety in an animal in need of such treatment comprising administering to said animal a therapeutically effective amount of a composition of claim 14.

16. A compound of claim 1 which is 1-(2-Chloro-4-thienyl)-3-(tetrahydro-1-methyl-4-oxo-1H-imidazol-2ylidene)urea.

17. A compound of claim 1 wherein Z is a 2- or 4-pyridinyl, thienyl, furanyl, 6-lower alkyl-2-pyridinyl or 2-halogen-4-thienyl radical.

18. A compound of claim 17, wherein said lower alkyl has 1 to 8 carbons and said halogen is chlorine, fluorine, bromine or iodine.

19. A compound of claim 18, wherein said lower alkyl is methyl and said halogen is chlorine.

20. A compound of claim 1, wherein the halogen of said 2-halogen-4-thienyl radical and of said halogen substituent on the furanyl radical is selected from the group consisting of chlorine, fluorine, bromine or iodine.

21. A compond of claim 1, wherein said pharmaceutically acceptable acid-addition salt is selected from the group consisting of a hydrochloride, hydrobromide, phosphate, sulfate, citrate, acetate or maleate.

22. A pharmaceutical composition for the treatment of anxiety comprising a therapeutically effective amount of a compound of claim 14 in combination with a pharmaceutically acceptable carrier or diluent therefore.

* * * * *

UNITED STATES PATENT AND TRADEMARK OFFICE
CERTIFICATE OF CORRECTION

PATENT NO. : 4,230,713
DATED : October 28, 1980
INVENTOR(S) : Thomas M. Bare

It is certified that error appears in the above—identified patent and that said Letters Patent is hereby corrected as shown below:

Columns 5 and 6 delete formula 5 as follows

" 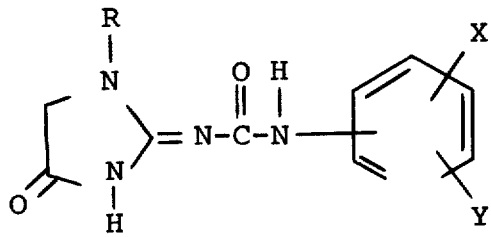 "

and insert therefor the following formula as formula 5

-- 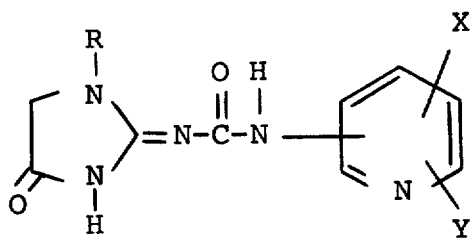 --

Column 8, line 55, delete ";b5.79;" and insert therefor --; 5.79;--.

Column 10, line 43, insert after the figure "2.6" the letter --g--.

Column 14, line 29, delete the word "not" and insert therefor --no--.

UNITED STATES PATENT AND TRADEMARK OFFICE
CERTIFICATE OF CORRECTION

PATENT NO. : 4,230,713

DATED : October 28, 1980

INVENTOR(S) : Thomas M. Bare

It is certified that error appears in the above—identified patent and that said Letters Patent is hereby corrected as shown below:

Column 13, line 50, delete the word "imidzol" and insert therefor --imidazol--.

Column 15, line 16, delete the words "of the present" and insert therefor --of presently--.

Column 15, line 53, delete the word "sticture" and insert therefor --stricture--.

Column 16, line 54, delete the figure "100" and insert therefor --1000--.

Column 18, Claim 16, delete the word "2ylidine)" and insert therefor --2-ylidine)--.

Signed and Sealed this

Third Day of February 1981

[SEAL]

Attest:

RENE D. TEGTMEYER

Attesting Officer

Acting Commissioner of Patents and Trademarks